United States Patent [19]

Ruttan

[11] Patent Number: 5,196,344
[45] Date of Patent: Mar. 23, 1993

[54] MILK SAMPLE PRESERVATIVE

[75] Inventor: Garry R. S. Ruttan, New Hamburg, Canada

[73] Assignee: D & F Control Systems, Inc., San Ramon, Calif.

[21] Appl. No.: 887,111

[22] Filed: May 19, 1992

Related U.S. Application Data

[63] Continuation of Ser. No. 485,583, Feb. 27, 1990, abandoned.

[51] Int. Cl.$^5$ .............................. A23C 3/08; G01N 1/00
[52] U.S. Cl. ............................................ 436/18; 422/1;
426/326; 426/330.2; 426/335; 426/532;
426/654; 436/23; 436/176; 514/31
[58] Field of Search ................ 436/18, 23, 176;
514/31; 422/1; 426/326, 330, 330.2, 335, 532, 654

[56] References Cited

U.S. PATENT DOCUMENTS

| | | | |
|---|---|---|---|
| 3,558,788 | 1/1971 | Clark et al. | |
| 3,996,386 | 12/1976 | Malkki et al. | 426/321 |
| 4,148,891 | 4/1979 | Smink | 514/31 |
| 4,536,494 | 8/1985 | Carter | 514/31 |
| 4,636,476 | 1/1987 | Brunt et al. | 436/23 |

FOREIGN PATENT DOCUMENTS

| | | |
|---|---|---|
| 1213773 | 11/1986 | Canada . |
| 1057131 | 2/1967 | United Kingdom . |
| 1193954 | 6/1970 | United Kingdom . |

OTHER PUBLICATIONS

Raab et al., Aerztl. Kosmetol., 10(6), Abstract, Chemical Abstract, 14, 109257f (1980).
Merck Index–Properties of natamycin.

Primary Examiner—Jill A. Johnston
Attorney, Agent, or Firm—Townsend and Townsend

[57] ABSTRACT

An antimicrobial composition for the preservation of milk samples required for analysis. The composition comprises 2-bromo-2-nitropropane-1,3-diol and natamycin, in effective amounts to prevent spoilage of the milk for a period of at least 5 to 10 days. The amount of 2-bromo-2-nitropropane-1,3-diol for a 50 ml milk sample is preferably 6–12 mg and the amount of natamycin is preferably 0.3–0.6 mg. The composition is preferably employed in the form of a tablet containing a suitable filler and usually other ingredients. In a method of preserving milk samples, the 2-bromo-2-nitropropane-1,3-diol and natamycin may be added separately or simultaneously (e.g. in admixture). The composition and method provide a way of preserving milk samples without the health problems associated with conventional preservatives such as dichromates and without the need to refrigerate the milk.

17 Claims, 3 Drawing Sheets

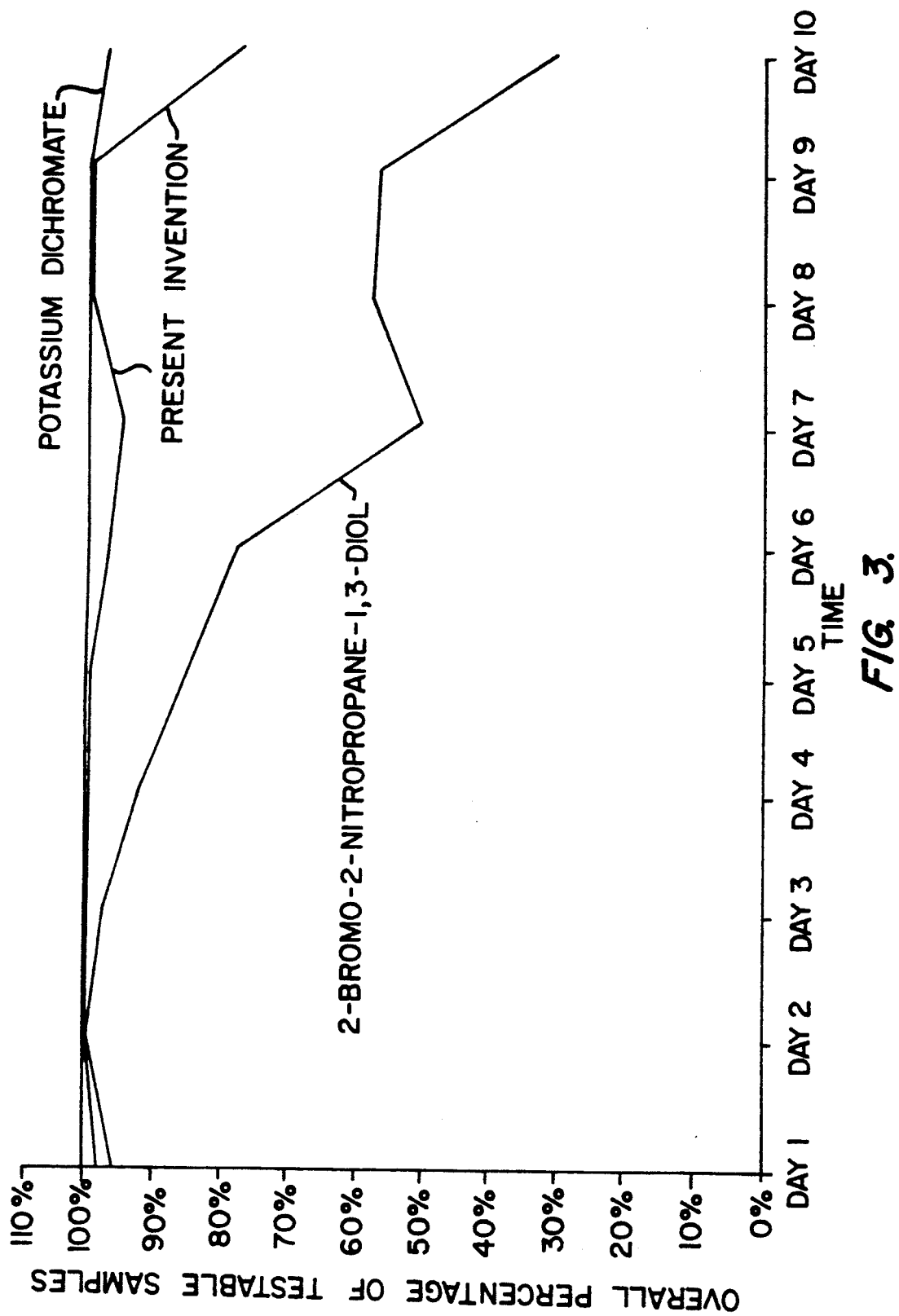

MILK SAMPLE PRESERVATIVE

This is a continuation of application Ser. No. 08/485,583 filed Feb. 27, 1990, now abandoned.

BACKGROUND OF THE INVENTION

I. Field of the Invention

This invention relates to preservatives used for preserving samples of milk intended for analysis and to methods of preserving such milk samples using preservatives of this type.

II. Description of the Prior Art

Dairy industries or governments in many countries conduct tests of milk output as part of the routine control procedures to ensure high quality, for the calculation of milk payment and for herd improvement. This testing, usually for fat, protein and lactose content, is usually carried out in centralized laboratories and there is often a considerable delay between the sample being taken and the test conducted. In view of this, and in view of the prohibitive cost of refrigerating the samples on a routine basis, it is necessary to preserve the milk with an efficient antimicrobial agent to prevent spoilage. Antimicrobial agents employed for this purpose must not interfere with the test procedure but must preserve the samples for at least 5 days and often up to 10 days.

The preservatives traditionally used for this, namely sodium or potassium dichromate, have come under increasing criticism in recent years owing to their tendency to cause allergic reactions in human skin that comes into frequent contact with the active ingredient. Other substances have been investigated as potential substitutes, and 2-bromo-2-nitropropane-1,3-diol has received considerable attention. When this compound is used in its traditional and well-established antibacterial concentration of 0.02% by weight, it performs efficiently as a sample preservative and does not interfere with the normal testing procedures. The compound is now used extensively in Europe and the U.S.A. for this purpose. One of the drawbacks of using this compound is that, at consistently high temperatures, the product becomes unstable and must be refrigerated to work properly. The use of 2-bromo-2-nitropropane-1,3-diol has therefore not proved to be entirely successful and there is still a need for an improved antimicrobial agent for preserving milk samples.

In U.S. Pat. No. 4,636,476 to Brunt et.al. issued on Jan. 13, 1987, a tablet for preserving milk samples is disclosed. The tablet comprises 2-bromo-2-nitropropane-1,3-diol and a water-soluble solid organic carboxylic acid. The presence of the organic acid is said to stabilize the 2-bromo-2-nitropropane-1,3-diol, thereby providing the tablet with adequate shelf life. However, milk samples preserved with these tablets do not appear to be significantly more stable than when the 2-bromo-2-nitropropane-1,3-diol itself is used.

OBJECTS OF THE INVENTION

An object of the present invention is to provide an improved antimicrobial agent for the preservation of milk samples.

Another object of the present invention is to provide an antimicrobial agent which has improved high temperature performance.

SUMMARY OF THE INVENTION

According to one aspect of the present invention, there is provided an antimicrobial composition for the preservation of milk samples, which comprises a mixture of 2-bromo-2-nitropropane-1,3-diol and natamycin.

According to another aspect of the invention, there is provided a method of preserving a milk sample for analysis, comprising adding to said milk sample an effective amount of the compound 2-bromo-2-nitropropane-1,3-diol and an effective amount of natamycin.

It is found that when natamycin is used in combination with 2-bromo-2-nitropropane-1,3-diol, the milk sample does not require refrigeration and in fact often works as well as, or better than, potassium dichromate used as a preservative.

BRIEF DESCRIPTION OF THE DRAWINGS

FIGS. 1, 2 and 3 are graphs showing the results of tests carried out as described in the Example.

DETAILED DESCRIPTION OF THE INVENTION

Figure 1:
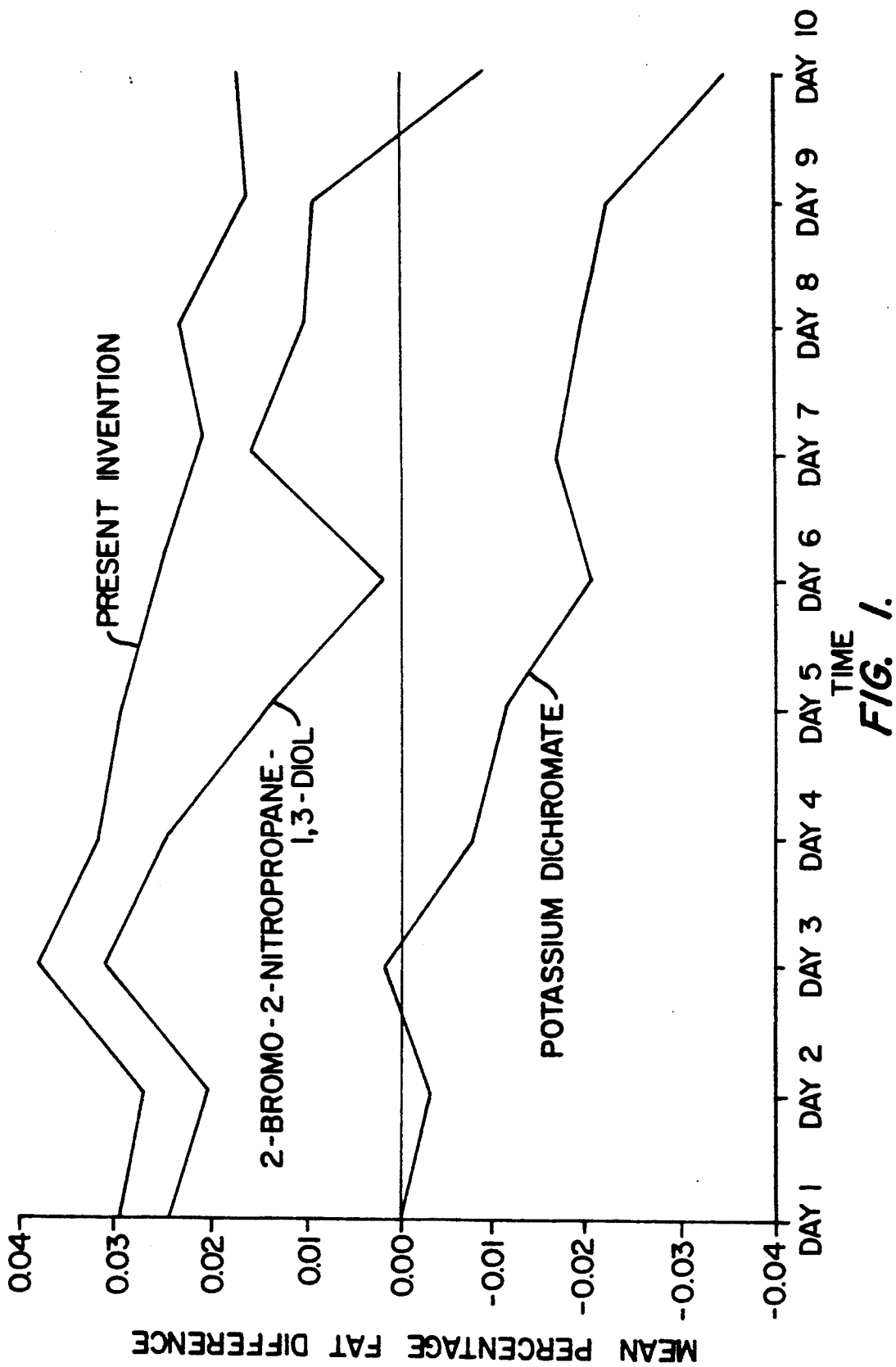

Natamycin is a known and commercially available yeast and mould inhibitor currently used to prevent the growth of yeasts and moulds in food products, such as cheese. More specifically, natamycin is a polyene antifungal antibiotic produced by *Streptomyces natalensis* and by *S. chattanoogensis* and is often referred to by other names, e.g. Pimaricin, antibiotic A 5283, tennecetin, CL 12625, Mycophyt, Myprozine, Natacyn and Pimafucin. Naturally, the present invention extends to compositions employing natamycin under any of its alternative names or designations. The antibiotic is currently available from a number of companies under various trademarks, e.g. from Gist-Brocades Food Ingredients, Inc. of King of Prussia, Pa. under the trademark DELVOCID. Further details of the antibiotic can be found in The Merck Index, Tenth Edition, 1983, published by Merck & Co., Inc., entry no. 6278, page 922.

The compound 2-bromo-2-nitropropane-1,3-diol is also widely commercially available for use in cosmetics etc. and is sold, for example, under the trademark BRONOPOL.

The ratio of 2-bromo-2-nitropropane-1,3-diol to natamycin employed in the present invention can be any ratio that is found to be effective, but normally weight ratios of 10–40:1 of 2-bromo-2-nitropropane-1,3-diol to natamycin, respectively, are found to be optimal. More preferably, the weight ratio is about 20:1.

In the milk testing business, a 50 ml (approximately 2 Imperial fluid ounces) milk sample is standard, so the concentration of the various materials added to the milk can be expressed as amounts required for the addition to 50 ml of milk. In the present invention, a preferred amount of 2-bromo-2-nitropropane-1,3-diol is 6 - 12 mg and a preferred amount of natamycin is 0.3–0.6 mg the preferred amounts of 2-bromo-2-nitropropane-1,3-diol and natamycin correspond to concentrations of from 120 µg/ml to 240 µg/ml and 6 µg/ml to 12 µg/ml, respectively. When 2-bromo-2-nitropropane-1,3-diol is used alone as in the prior art, it is usual to employ about 12 mg. If this amount is used in the present invention, 0.6 mg of natamycin is required in order to provide the preferred ratio of 20:1. However, this makes the preservative treatment quite expensive and it is a particular advantage of the present invention that the concentration of 2-bromo-2-nitropropane-1,3-diol can be reduced and still be effective when it is used in combination with natamycin. Therefore, it is found that the concentration of 2-bromo-2-nitropropane-1,3-diol can be reduced to about 6 mg and the concentration of natamycin consequently reduced to about 0.3 mg in order to maintain the 20:1 weight ratio.

It is most convenient in the present invention to produce a composition of 2-bromo-2-nitropropane-1,3-diol and natamycin in the form of a solid mixture and preferably a solid tablet. A tablet containing the required amounts of the two active ingredients can then be simply added to a 50 ml milk sample and dissolved. Tablets of this kind may contain other ingredients, e.g. a filler such as sodium chloride, a granulating agent such as CARBOWAX 8000 (trademark) or KLUCEL E.F. (trademark), a diluent for the granulating agent such as isopropyl alcohol, a colouring agent (to prevent accidental ingestion of treated milk) such as FD and C YELLOW #6, etc.

The composition of the invention is preferably formulated into tablets having a weight of about 20 mg. This size of tablet is preferred because it disintegrates quickly, thus allowing it to begin working more quickly, and the filler which would be needed to make a larger tablet could have adverse effects on the infrared equipment commonly used for the testing procedure.

Particularly preferred tablets can be prepared by passing BRONOPOL (6.00 mg) and sodium chloride (12.48 mg) through a 40 Tyler mesh screen, blending the screened BRONOPOL and sodium chloride with DELVOCID (0.30 mg) and FD&C Yellow #6 (1.00 mg) until uniform, dissolving KLUCEL E.F. (0.2 mg) in isopropyl alcohol (0.3 mg) and wetting the blend with the resulting solution, drying the mixture and passing it through a 40 Tyler mesh screen, adding CARBOWAX 8000 and blending and tableting the resulting blend using a 3 mm flat face tool at a weight of 20 mg. The weights in brackets represent the weights of the ingredients per tablet, although of course larger batches of the composition would normally be produced.

Despite the preferred use of solid mixtures in the form of tablets, the two active ingredients of the invention could be used in other forms (e.g. in solution in suitable solvents) and could, if desired, be added to the milk separately.

Without wishing to be limited to any particular theory, it is thought that the combined use of the active materials of the present invention may be effective for the following reasons. The natamycin may remain on the top of the milk sample and does not mix with the milk. It is therefore ideally placed to control the growth of yeast and mould which commences at the milk surface. The 2-bromo-2-nitropropane-1,3-diol, on the other hand, mixes with the milk and acts as an antibacterial agent. The control of the growth of the yeast and mould at the surface may help to eliminate bacteria in the milk and thus enhances the action of the 2-bromo-2-nitropropane-1,3-diol.

The invention is illustrated in more detail by the following non-limiting Example.

EXAMPLE

In this Example, the effectiveness of a composition according to the present invention is compared with that of 2-bromo-2-nitropropane-1,3-diol used alone and that of potassium dichromate, the conventional preservative for milk samples.

The composition of the invention used in the Example was a tablet containing 6 mg of 2-bromo-2-nitropropane-1,3-diol and 0.3 mg of natamycin.

A total of seven sets of identical milk samples (50 ml each) were collected from each of thirty dairy herds made up of 19 Holstein herds, 4 Jersey herds, 4 Guernsey herds and 3 Ayrshire herds. Each set of samples consisted of groups of 10 identical samples preserved with the different types of preservatives mentioned above. The first set of samples were shipped with the regular herd test. The remaining six sets of samples were shipped on consecutive days thereafter.

All of the samples involved in this trial were analyzed at a commercial milk analysis centre (D.H.I. Corporation of Ontario, Canada). The samples were tested for butterfat and protein content. All samples were tested on the day on which they arrived. To eliminate day to day instrument variation, all samples were tested on the same instrument at the same daily time throughout the trial. Control samples were also used to monitor the amount of day to day instrument variation.

In the case of the butterfat tests (which are the most important because it forms the basis on which the farmers are paid), the composition of the invention resulted in samples which were stable over the entire 10 day period. The 2-bromo-2-nitropropane-1,3-diol alone, however, gave samples which were less stable after Day 4, indicating that refrigeration would be required. Potassium dichromate showed a gradual deterioration from Day 4 on.

The protein results were similar for all of the preservatives, but this is not significant because protein is not used as a basis for payment purposes.

The 2-bromo-2-nitropropane-1,3-diol alone also gave rise to a large number of non-testable samples after Day 3 resulting from soured, oiled off or churned conditions, but no noticeable deterioration occurred in the case of the other preservatives until Day 9.

Figure 2:
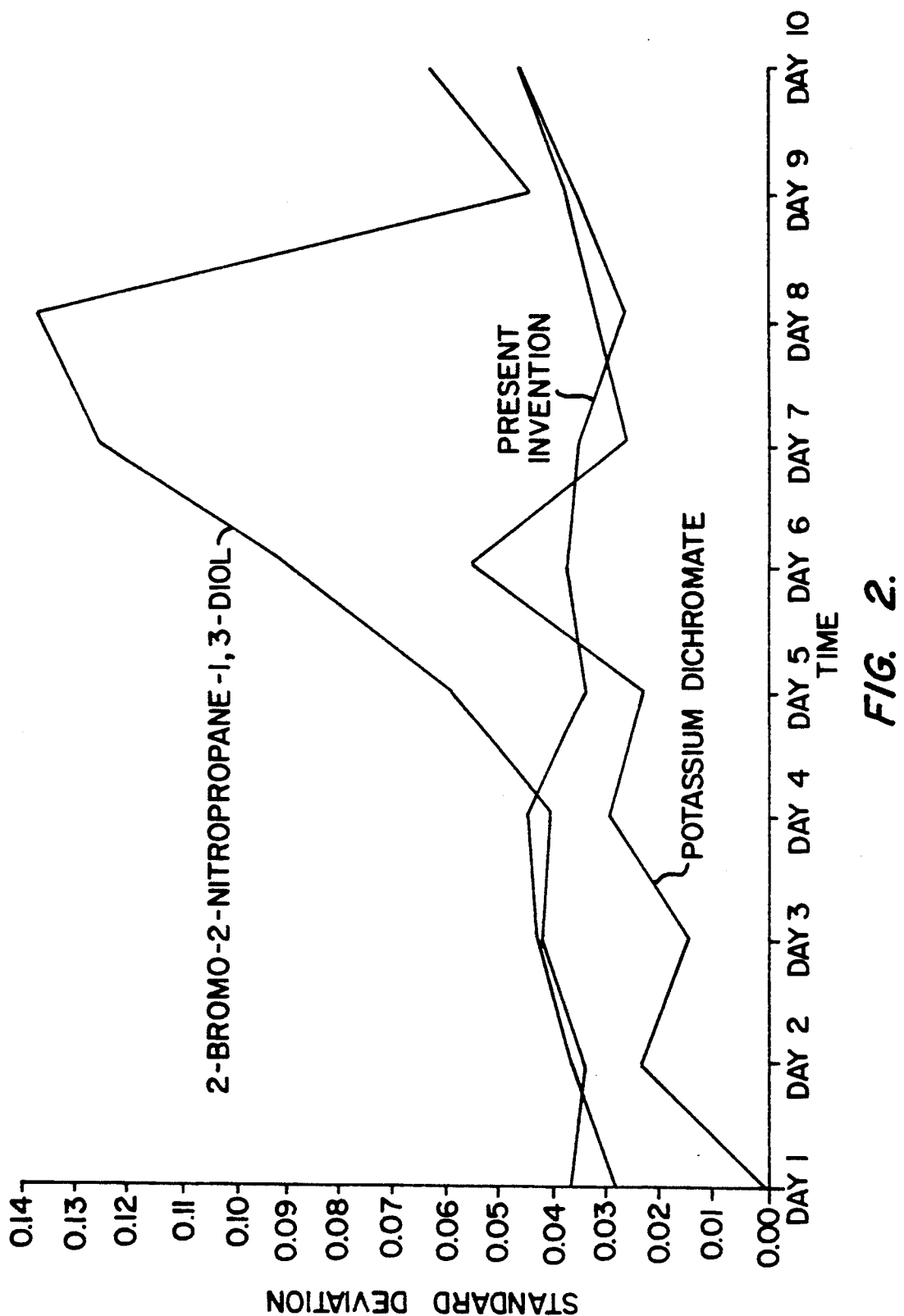

FIGS. 1, 2 and 3 of the accompanying drawings are graphs showing the results of the tests mentioned above, with FIG. 1 showing the overall mean butterfat percentage difference, FIG. 2 showing the standard of deviation of the test results and FIG. 3 showing the overall percentage of testable samples. The superiority of the composition of the invention compared with 2-bromo-2-nitropropane-1,3-diol alone is apparent from the graphs.

What I claim is:

1. A solid antimicrobial composition for the preservation of milk samples, which comprises a mixture of 2-bromo-2-nitropropane-1,3- diol and natamycin in a ratio by weight of about 10–40:1, respectively.

2. A composition according to claim 1 wherein the ratio by weight of 2-bromo-2-nitropropane-1,3- diol to natamycin is about 20:1.

3. A composition according to claim 1, containing at least one additional material selected from the group consisting of a filler, a granulating agent, a diluent and a colouring agent.

4. A composition according to claim 1, in the form of a tablet.

5. A composition according to claim 4 wherein the tablet contains amounts of 2-bromo-2-nitropropane-1,3-diol and natamycin suitable for the preservation of about 50 ml of milk.

6. A composition according to claim 5 containing 6–12 mg 2-bromo-2-nitropropane-1,3- diol and 0.3–0.6 mg natamycin.

7. A composition according to claim 5 containing about 6 mg 2-bromo-2-nitropropane-1,3- diol and about 0.3 mg natamycin.

8. A method of preserving a milk sample for analysis comprising adding to said milk sample a solid composition comprising 6–12 mg of 2-bromo-2-nitropropane-1,3- diol and 0.3–0.6 mg of natamycin for each 50 ml of milk.

9. A method according to claim 8 wherein, for each 50 ml of milk, the amount of 2-bromo-2-nitropropane-1,3- diol added is about 6 mg and the amount of natamycin added is about 0.3 mg.

10. A method according to claim 8, or claim 9 wherein the 2-bromo-2-nitropropane-1,3- diol and natamycin are added simultaneously.

11. A method according to claim 10 wherein the 2-bromo-2-nitropropane-1,3- diol and natamycin are added in the form of a mixture.

12. A method according to claim 8, wherein the 2-bromo-2-nitropropane-1,3- diol and natamycin are added separately to the milk.

13. A solid tablet suitable for the preservation of a 50 ml sample of milk for analysis, comprising 6–12 mg of 2-bromo-2-nitropropane-1,3- diol and 0.3–0.6 mg of natamycin.

14. A table according to claim 13 further comprising at least one additional material selected from the group consisting of a filler, a granulating agent, a diluent and a colouring agent.

15. A method of preserving a milk sample for analysis, said method comprising:
adding to the milk sample a tablet comprising amounts of 2-bromo-2-nitropropane-1,3- diol and natamycin which provide concentrations of 120 $\mu$g/ml to 240 $\mu$g/ml and 6 $\mu$g/ml to 12 $\mu$g/ml respectively and are sufficient to inhibit degradation of the milk sample by bacteria, yeast, and mold for a period of 10 days without refrigeration, wherein the presence of the natamycin does not significantly interfere with the measurement of butterfat and protein.

16. A method for analyzing a milk sample, said method comprising:
adding to the milk sample amounts of 2-bromo-2-nitropropane-1,3- diol and natamycin which provide concentrations of 120 $\mu$g/ml to 240 $\mu$g/ml and 6 $\mu$g/ml to 12 $\mu$g/ml respectively and are sufficient to inhibit the growth of bacteria, yeast, and mold for a period of 10 days without refrigeration; and
analyzing the milk sample for butterfat and protein content, using infrared analysis wherein the presence of natamycin does not significantly interfere with such analysis.

17. A tablet comprising:
6 to 12 mg of 2-bromo-2-nitropropane-1,3- diol;
0.3 to 0.6 mg of natamycin;
a coloring agent; and
a filler.

* * * * *